(12) United States Patent
Vitik et al.

(10) Patent No.: US 6,194,397 B1
(45) Date of Patent: Feb. 27, 2001

(54) PHOSPHORUS CONTAINING CYTISINE DERIVATIVES

(76) Inventors: Andrej Zinovyevich Vitik, 14 Mikroraion, 8-22; Arstan Maulenovich Gazaliev, Bulvar Mira, 18-47, both of Karaganda, 470055 (KR); Alexander Evgenyevich Gulyaev, ul.Poletaeva, 16-9, Karaganda, 470032 (KZ)

(*) Notice: Subject to any disclaimer, the term of this patent is extended or adjusted under 35 U.S.C. 154(b) by 0 days.

(21) Appl. No.: 09/194,176

(22) PCT Filed: May 20, 1996

(86) PCT No.: PCT/KZ96/00002

§ 371 Date: Oct. 12, 1999

§ 102(e) Date: Oct. 12, 1999

(87) PCT Pub. No.: WO97/44343

PCT Pub. Date: Nov. 27, 1997

(51) Int. Cl.[7] .................. A61K 31/675; C07F 9/6561
(52) U.S. Cl. ............................... 514/80; 546/23
(58) Field of Search .................. 546/23; 514/80

(56) References Cited

PUBLICATIONS

Chemical Abstracts, vol. 66(5),abst. No. 18,852(b), Jan. 1967.*
Chemical Abstracts, vol. 125 (19),abst. No. 248,202f, Nov. 4, 1996.*
"Silibinin", Mashkovsky M.D. Medicinal remedies, Vilnius, v.1, 1994, p.450.
"Essentiale", Mashkovsky M.D. Medicinal remedies, Vilnius, v.1, 1994, p.40.

* cited by examiner

Primary Examiner—Alan L. Rotman
(74) Attorney, Agent, or Firm—Rader, Fishman & Grauer PLLC

(57) ABSTRACT

Claimed are newly synthesized phosphorus containing cytisine derivatives of the general formula

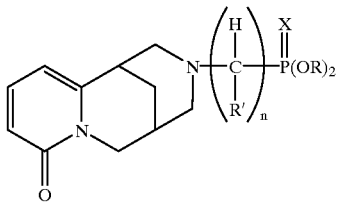

wherein
  n is 0 or 1;
  X is O or S;
  R=$CH_3$;
  $C_2H_5$;
  $C_3H_7$;
  1-$C_3H_7$;
  $C_4H_9$;
at
  n=1: X=O
  R=$CH_3$
  $R^1$=1—$C_3H_7$;
  $C_6H_5$;
  $CH_3$—O—$C_6H_4$—;
with a proviso that n is 1, X is O.

It is shown that some of the synthesized compounds exhibit substantial hepatoprotective and antienzyme activity.

1 Claim, No Drawings

US 6,194,397 B1

PHOSPHORUS CONTAINING CYTISINE DERIVATIVES

CROSS REFERENCE

This application is a 371 of PCT/KZ96/00002 filed May 20, 1996.

BACKGROUND OF THE INVENTION

1. Technical Field

The invention is related to new chemical compounds, in particular to phosphorus containing cytisine derivatives showing their hepatoprotective and antienzyme activities.

2. Background Art

It is known that alkaloid cytisine (1) extracted firstly from the seeds of broom and thermopsis is now widely used in the medical practice in a state of 0.15% water solution (cytiton) as an analeptic agent (Mashkovsky, M. D., "Medicine remedies", M., 1977, v.1, p.123).

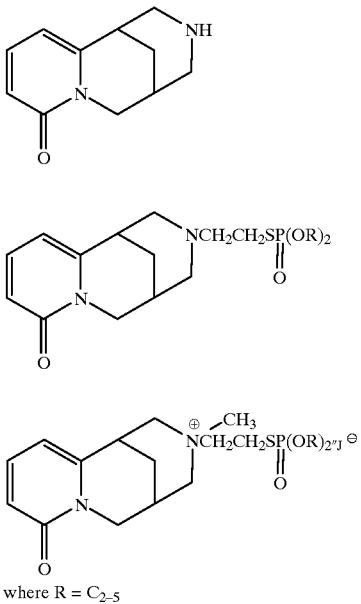

where R = $C_{2-5}$

A typical property of cytisine is its ability to arouse breathing that is connected with refectory stimulation of breathing center by intensified impulses coming from carotid balls. Simultaneous stimulation of sympathetic knots and adrenal glands leads to the rise of arterial pressure. In this connection, cytisine is recommended to be used in case of the stopping of breathing and heart activity at intoxication.

Cytisine is widespread in nature. It has been found in many plants and its extraction from a plant raw material by an ion exchange method is the main industrial way to obtain cytisine.

Synthesis of phosphorus containing N-[β-(dialkocsiphosphenyl) mercaptoethyl] cytisines (2) and their iodine methylates (3) has been described in works (Reports of the Uzbek SSR Academy of Sciences, 1978, No. 9, pp. 39–42; Reports of the Uzbek SSR Academy of Sciences, 1977, No. 7, pp. 40–43).

Authors have shown that all synthesized compounds have the irreversible inhibiting activity in a case of acetylcholinesterase and display the effect of selective inhibition of the butyrylcholinesterase catalytic activity.

Authors are aware of no evidences of other phosphorus containing cytisine derivatives in literature.

SUMMARY OF THE INVENTION

In connection with that the initial cytisine alkaloid displays considerable biological activity, one can assume that other phosphorus containing cytisine derivatives will also be of interest from this point of view.

An object of the present invention is to obtain new phosphorus containing cytisine derivatives that in particular have increased biological activity.

The object is attained by providing phosphorus containing cytisine derivatives of the general formula:

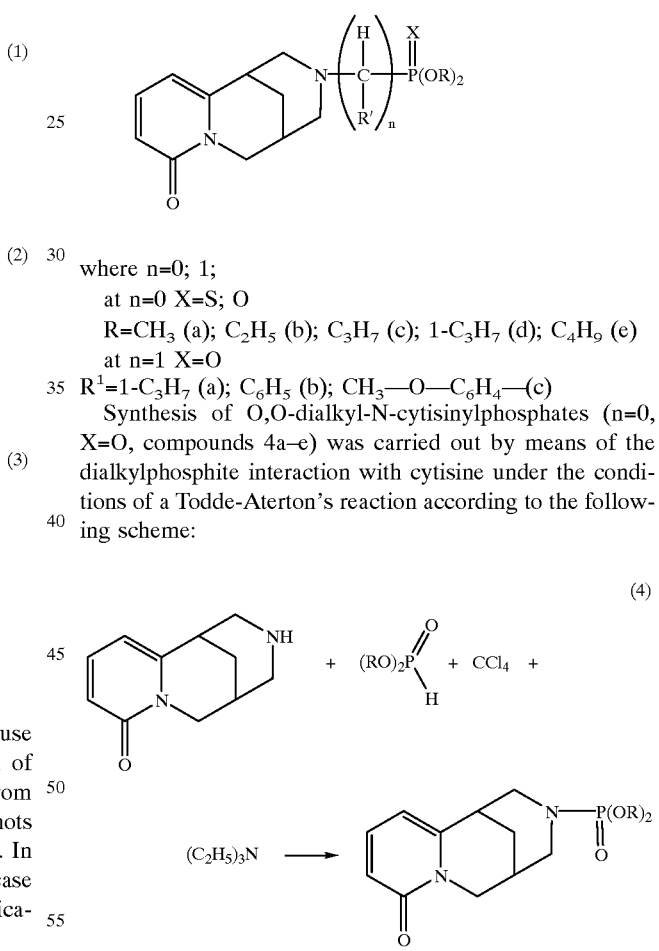

where n=0; 1;
  at n=0 X=S; O
    R=$CH_3$ (a); $C_2H_5$ (b); $C_3H_7$ (c); 1-$C_3H_7$ (d); $C_4H_9$ (e)
  at n=1 X=O
    $R^1$=1-$C_3H_7$ (a); $C_6H_5$ (b); $CH_3$—O—$C_6H_4$—(c)

Synthesis of O,O-dialkyl-N-cytisinylphosphates (n=0, X=O, compounds 4a–e) was carried out by means of the dialkylphosphite interaction with cytisine under the conditions of a Todde-Aterton's reaction according to the following scheme:

The synthesis of O,O-dialkyl-N-cytisinylthiophosphates (n=0, X=S, compounds 5a–e) was carried out in two stages. In the first stage, during the cytisine interaction with dialkylchlorphosphite (the synthesis was described in E. V. Nifantyev, "Chemistry of phosphorus containing compounds", M. Science, 1983, p.85), the interaction being performed in the benzene medium in the flow of dry argon and in the presence of triethylamine, an intermediate O,O-dialkyl-N-cytisinylphosphite is formed that then reacts with an equimolar amount of elementary sulfur giving O,O-dialkyl-N-cytisinylthiophosphate.

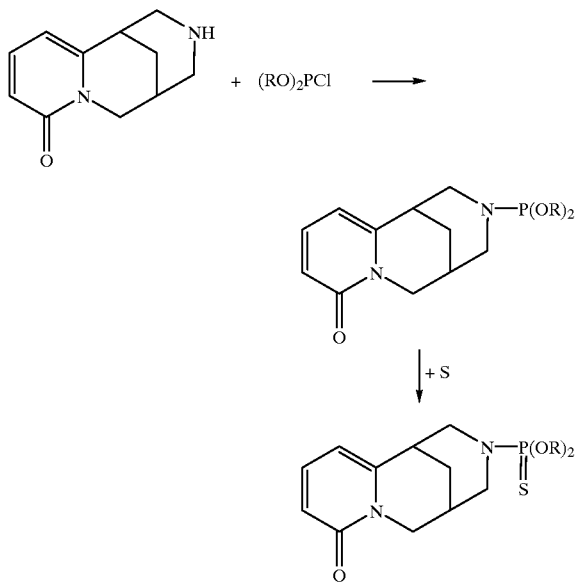

Dimethyl-(N-cytisinyl) alkyl (aryl) phosphonates (n=1, X=O, R=CH$_3$, compounds 6a–c) have been obtained by means of the cytisine interaction with aldehydes and dimethylphosphite under the conditions of a Kabachnic-Fild's reaction

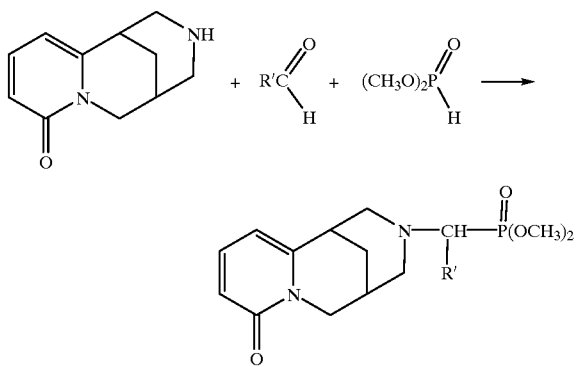

PREFERRED EMBODIMENTS OF THE INVENTION

The following examples explain the invention in more detail, without restricting it by this.

EXAMPLES

1. Synthesis of O,O-dimethyl-N-cytisinylphosphate (4a).

A mixture containing 2.86 g (0.026 moles) of dimethylphosphite and 15.5 ml (0.16 moles) of carbon tetrachloride in 100 ml of benzene is placed into a flask and when being stirred is added dropwise with a mixture containing 5 g (0.026 moles) of cytisine and 2.63 g (0.026 moles) of triethylamine in 230 ml of dry benzene, the adding being performed at such a rate that the temperature of the solution not exceed 20° C.

After the adding dropwise is over, the reaction mixture is stirred at a room temperature for 6 hours. Precipitated crystals of hydrochloric triethylamine are filtered out, and the solvent is distilled off in a vacuum evaporator. A crystallized substance (recrystallization from benzene) in the amount of 5.64 g (the yield is 72.5% of the theoretical one) with the melting point $T_m$ 158–159° C. is obtained.

IR-spectrum, ν, cm$^{-1}$: 1270(P—O). 1050(P—O—C), 830 (P—N—C), 1658(N—CO). EPR spectrum, δ, m. d. 6.23d. (IH, CH$_\alpha$, $^3J_{HH}$ 5.0 Hz), 7.23d.d. (IH, CH$_\beta$, $^3J_{HH}$ 3.2 Hz), 6.12d. (IH, CH$_\gamma$) 3.34 d (6H, CH$_3$O, $J_{CH3P}$ 13.2H$_2$). NMR $^{31}$P: $\delta_P$=9.1 m.d. Found, %: C 52.05; H 6.24; N 9.30; P 10.36; C$_{13}$H$_{19}$N$_2$O$_4$P Calculated, %: C 52.36; H 6.37; N 9.40; P 10.40.

According to the data of X-ray diffraction analysis, the coordination of an [atom of phosphorus in a molecule of O,O-dimethyl-N-cytisinylphosphate is distorted tetrahedral, usual for phosphate groupings. A dihydropyridine cycle is flat to an accuracy of ±0.01 Å, with a carbonyl atom of oxygen deviating negligibly (by 0.07 Å) from this plane.

A tetrahydropyridine cycle takes a seat conformation ($\Delta C^8_S$ 2.7°), with the bridging atom C deviating from an average plane of other ones by 0.75 Å. A pyperidine cycle has the almost ideal seat conformation ($\Delta C^8_S$ 0.5°). Methyl CH$_3$ groups have a Rosh-orientation in respect to P—O and P—O bonds correspondingly.

Other compounds 4b–c of this row have been obtained similarly (see Table 1).

2. Synthesis of O,O-dimethyl-N-cytisinylthiophosphate (5a).

5 g (0.026 moles) of cytisine and 2.63 g (0.026 moles) of triethylamine in 200 ml of absolute benzene are placed into a flask. 3.33 g (0.026 moles) of dimethylchlorphosphite are added to the mixture during intensive stirring thereof in the flow of dry argon and at a room temperature. The mixture is stirred for 5 hours. A precipitated residue of triethylamine hydrochloride is filtered out by means of flushing it by portions of absolute benzene. The filtrate and calculated amount of 0.83 g (0.026 moles) of sulfur are placed into the flask and the stirring is continued for another 2 hours at the room temperature. Then, the mixture is distilled off in a rotor evaporator and the precipitate is recrystallized from benzene. 8.01 g (yield is 97%) of a crystallized substance with $T_m$ 164–165° C. are obtained.

IR-spectrum, ν, cm$^{-1}$: 1030 (P—O—C), 1670 (N—CO), 820 (P—S). EPR spectrum, δ, m.d. 6.23d (IH, CH$_{60}$, $^3J_{HH}$ 6.0 Hz); 7.16d.d. (IH, CH$_\beta$, $^3J_{HH}$ 5.8 Hz); 5.8d. (IH, CH$_\gamma$), 3.40d (6H, CH$_3$O, $J_{CH_3P}$ 12.0 Hz). NMR $^{31}$P: δp=10.22m.d. Found, %: C 49.91; H 6.13; N 8.87; P 9.69; C$_{13}$H$_{19}$N$_2$O$_3$SP Calculated, %: C 49.68; H 6.05; N 8.91; P 9.87.

Compounds 5$_{b-e}$ of this row have been obtained similarly. The results are presented in Table 1.

3. Synthesis of dimethyl-2-(N-cytisinyl)-2-isobutylphosphonate (6a).

A mixture containing 3.8 g (0.02 moles) of cytisine, 1.24 g (0.02 moles) of isobutyric aldehyde, 2.2 g (0.02 moles) of dimethylphosphite and a catalytic amount of 18-crown-6 in 100 ml of benzene is boiled for 3 hours with the simultaneous distillation of water formed in the course of the reaction. After distilling the solvent when the reaction is over, a residue is washed by hexane and recrystallized from a benzene-ether mixture. 5.52 g (yield is 78.1%) of a crystallized substance with melting point $T_m$ 138° C. are obtained.

IR-spectrum, ν, cm$^{-1}$: 1220 (P—O), 1070 (P—O—C). EPR spectrum, δ, m.d. 6.72d (IH, CH$_\alpha$, $^3J_{HH}$ 8.6 Hz); 7.10d.d. (IH, CH$_\beta$, $^3J_{HH}$ 6.4 Hz); 6.51d (IH, CH$_\gamma$), 3.31 d (6H, CH$_3$O, $J_{CH_3P}$ 12.6 Hz). 0.50d. (3H, CH$_3$—C), 0.87D. (3H, CH$_3$—C). Found, %: C 57.70; H 7.72; N 8.03; P 8.67; $C_{17}H_{27}N_2O_4P$ Calculated, %: C 57.56; H 7.58; N 7.90; P 8.52

Other compounds $6_{b-c}$ of this row have been obtained similarly (see Table 1).

INDUSTRIAL APPLICABILITY

Biological activity of state compounds.

Pharmacological investigations conducted have shown the synthesized compounds to display hepatoprotective and antienzyme activities.

I. The study of hepatoprotective activity.
  1. Acute toxicity of the compound.

An average lethal dose $LD_{50}$ was determined on white randombred mice (320 head, by 18–20 g each). The preparation was injected once intravenously in the physiological solution or given perorally in a 1% starch suspension. An observation period was 14 days. General state of animals was examined every day, the animals were weighted three times during the observation period, deceased animals were dissected and macroscopic description was done. The determination of $LD_{50}$ was carried out by the method of probit analysis.

As a result of the conducted experiments, it has been found that $LD_{50}$=4300 mg/kg (3200–5800) at the peroral intake of the compound, and $LD_{50}$=1800 mg/kg (1250–2550) at the intravenous injection. An average arithmetical value and confidence semi-interval at P=95% have been presented.

2. Hepatoprotective activity at the acute hepatitis in rats.

According to pharmacologists, the most effective hepatoprotective agent is now the preparation "Essentialle" (FRG) that was used in the following experiments as a reference preparation. This preparation is a complex set of substances and contains a sum of flavonoids, phospholipins, nicotineamide and various vitamins.

A study of hepatoprotective activity of the stated preparation at acute toxic hepatitis was performed on four groups of white randombred rat males weighing 120–150 grams, by 10 specimens in each of the groups.

The first group. Animals were subjected to an intravenous injection of 0.1 ml of an isotonic solution of sodium chloride, and then in an hour they were subjected to an intraperitoneal injection of 0.4 ml of petroleum jelly.

The second group. Animals were subjected to an intravenous injection of 0.1 ml of an isotonic solution of sodium chloride, and then in an hour they were subjected to an intraperitoneal injection of 0.4 ml of 40% solution of hepatotropic poison—carbon tetrachloride in petroleum jelly.

The third group. Animals were subjected to an intravenous injection of 0.1 ml of the "Essentialle" solution (50 mg/kg), and then in an hour they were subjected to an intraperitoneal injection of 0.4 ml of a 40% $CCl_4$ solution in petroleum jelly.

The fourth group. Animals were subjected to an intravenous injection of 0.1 ml of a water solution of the stated substance (50 mg/kg), and then in an hour they were subjected to intraperitoneal injection of 0.4 ml of a 40% $CCl_4$ solution in petroleum jelly.

All injections were repeated once a day for the period of four days, and the animals were decapitated thereafter under ether narcosis.

Hepatoprotective activity of the stated preparation and the reference preparation at poisoning rats with carbon tetrachloride was estimated by the change of biochemical and hystological factors characterizing the rate of damage (destruction) of cells at poisoning.

Investigated were enzyme activity of alaninaminotranspherase (ALAT) and the level of total bilirubin in blood, erythrocyte chemiluminescence and morphometrically volumetric portion of necroses, intralobule infiltration, regenerating and dystrofied cells in sections of a liver tissue.

At studying chemiluminescence, the erythrocytes extracted from blood were suspended in an isotonic sodium chloride solution (by 1 ml of a 10% erythrocyte suspension in a sample), a glow was stimulated with 0.1 ml of 5% $H_2O_2$, and average arithmetic values of an integral area under the curve of chemiluminescence were determined.

| Group | ALAT mmole hour/liter | Bilirubin micromole/liter | Area under the curve of chemiluminescence |
|---|---|---|---|
| 1 | 215 ± 8.1 | 8.06 ± 0.4 | 4.34 |
| 2 | 1828 ± 34.6 | 31.12 ± 1.09 | 9.395 |
| 3 | 1291 ± 10.5 | 20.84 ± 0.25 | 7.35 |
| 4 | 445.4 ± 11.7 | 12.90 ± 0.32 | 5.386 |

| Group | Dystrophy % | Necrosis % | Infiltration % | Regeneration % |
|---|---|---|---|---|
| 1 | 2.6 | 0.2 | 0.35 | 1.4 |
| 2 | 20.5 | 4.3 | 0.6 | 0.652 |
| 3 | 12.8 | 0.9 | 0.4 | 1.03 |
| 4 | 8.2 | 0.5 | 0.3 | 1.48 |

The data presented demonstrates that the stated substance has hepatoprotective activity at intoxication in rats with carbon tetrachloride, the substance acting more intensively than the "Essentsialle" preparation used as the reference.

3. The effect of the stated substance on the survival rate of mice at intoxicating them with hepatotropic poison.

To study the effect of the preparation on mouse survival rate at intoxicating them with hepatotropic poison, white randombred mice were used, specifically males weighing 18–20 grams, three groups by 10 mice each.

Animals of the first group were subjected to intraperitoneal injections of 0.1 ml of an isotonic sodium chloride solution. Animals of the second group were subjected to intravenous injections of 0.1 ml of the "Essentsialle" solution in a dose of 50 mg/kg. Animals of the third group were subjected to intraperitoneal injections of 0.1 ml solution of the stated substance in a water solution (100 mg/kg).

In an hour after the first injection, all animals were subjected to intraperitoneal injections of 0.1 ml of a 50% carbon tetrachloride solution in petroleum jelly.

The injections were made once. An observation period was 5 days. The survival rate in five days was the following:

| Group | Amount of survived animals | The survival rate |
|---|---|---|
| 1 | 0 | 0 |
| 2 | 2 | 20 |
| 3 | 8 | 80 |

The results obtained show that proposed compound protects animals from death at intoxicating them with hepatotropic poison to the greater extent than the "Essentsialle". Thus, we have found that the compound had moderate toxicity and its hepatoprotective action in the experiments in animals considerably exceeds the effect of the "Essentsialle" preparation.

II. The study of antienzyme activity.

Upon investigating antienzyme activity of synthesized compounds, their interactions with acethylcholinestherase (ACE) and butirylcholinestherase (BCE) were studied. ACE from human blood erythrocytes with specific activity of 1.2 Unit/mg and BCE from horse blood serum with specific activity of 9,6 Unit/mg were used. The ACE and BCE activities were determined by the Ellman calorimetric method at 25° C. in a 0.2M Na-phosphate buffer, pH=7.5. Acethylthiocholine iodide of the Czechoslovak company "Chemapol" was used as a substrate. Efficiency of reversible inhibitors was determined by the method of A.P. Brestkin and characterized by the value of a generalized inhibitory constant ($\bar{K_i}$) that at the mixed type of inhibition is related to competitive ($K_i$) and competitiveless ($K^1_i$) components with the equation:

$$1/\bar{K_i} = 1/K_i + 1/K^1_i$$

Activity of P450 cytochrome was determined by two methods: by the rate of hydroxylation of 3.4-benz/a/pyrene, by means of fluorimetric determination of 4-hydroxybenz/a/pyrene that was being formed, and by the rate of diethylation of 7-ethoxycoumarin by using of fluorimetric determination of 7-hydroxycoumarin that was being formed.

Inhibiting influence of the substances under the study on P450 cythochrome was estimated by values $pJ_{50}$ that are inverse logarithms of the agent concentration causing decrease of the activity by 50%.

It has been found that cytisinylphosphates and cytisinylthiophosphates are ACE inhibitors of medium power and quite effective BCE inhibitors. The most selectivity relative to BCE was observed for thiophosphate derivatives (pK1=6.7 and pK1=6.1, correspondingly).

Also revealed were power inhibitors of p450 cythochrome that are promising for practical application, the compounds with $pJ_{50}=5.55$ and $pJ_{50}=5.70$ being among them.

TABLE 1

Physical and chemical constants and the element analysis results of stated compounds.

| | | | Found, % | | | | Gross | Calculated, % | | | | |
|---|---|---|---|---|---|---|---|---|---|---|---|---|
| Compound | Tm, ° C. | $n^{20}$ | C | H | N | P | Formula | C | H | N | P | Yield, % |
| 4a | 158–159 | — | 52.08 | 6.27 | 9.48 | 10.26 | C13H19N2O4P | 52.36 | 6.37 | 9.40 | 10.40 | 72.5 |
| 4b | — | 1.5258 | 55.39 | 7.13 | 8.65 | 9.66 | C15H23N2O4P | 55.21 | 7.05 | 8.59 | 9.51 | 68.4 |
| 4c | — | 1.5027 | 57.72 | 7.69 | 7.82 | 8.83 | C17H27N2O4P | 57.62 | 7.62 | 7.91 | 8.75 | 69.7 |
| 4d | 115–116 | — | 57.81 | 7.74 | 7.87 | 8.86 | C17H27N2O4P | 57.62 | 7.62 | 7.91 | 8.75 | 70.5 |
| 4e | — | 1.4836 | 59.77 | 8.19 | 7.28 | 8.20 | C19H31N2O4P | 59.68 | 8.11 | 7.33 | 8.11 | 63.8 |
| 5a | 164–165 | — | 49.91 | 6.18 | 8.87 | 9.69 | C13H19N2O3PS | 49.68 | 6.05 | 8.91 | 9.87 | 97.0 |
| 5b | 99–100 | — | 52.72 | 6.79 | 8.14 | 9.17 | C15H23N2O3PS | 52.63 | 6.72 | 8.19 | 9.06 | 92.5 |
| 5c | — | 1.5486 | 55.24 | 7.41 | 7.50 | 8.43 | C17H27N2O3PS | 55.13 | 7.30 | 7.57 | 8.38 | 87.3 |
| 5d | — | 1.5463 | 55.19 | 7.38 | 7.49 | 8.47 | C17H27N2O3PS | 55.13 | 7.30 | 7.57 | 8.38 | 75.1 |
| 5e | — | 1.5446 | 57.38 | 7.86 | 7.01 | 7.91 | C19H31N2O3PS | 57.28 | 7.79 | 7.04 | 7.79 | 82.0 |
| 6a | 137–139 | — | 57.70 | 7.72 | 8.03 | 8.67 | C17H27N2O4P | 57.56 | 7.58 | 7.90 | 8.52 | 78.1 |
| 6b | 190–192 | — | 61.87 | 6.47 | 7.19 | 7.99 | C20H25N2O4P | 61.85 | 6.44 | 7.21 | 7.98 | 85.2 |
| 6c | 186–188 | — | 60.18 | 6.74 | 6.56 | 7.37 | C21H28N2O5P | 60.14 | 6.68 | 6.68 | 7.39 | 87.0 |

What is claimed is:

1. A method of protecting the liver against hepatotropic toxins comprising administering to a patient in need of said treatment an effective amount of a phosphorus-containing cytisine derivative of the following formula

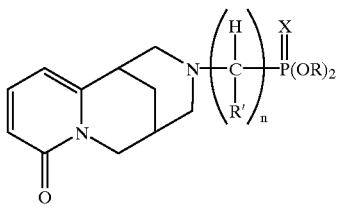

wherein (n) is 0 or 1; X is =S or =O; R is —CH$_3$, —C$_2$H$_5$, —C$_3$H$_7$, —CH—(CH$_3$)$_2$ and C$_4$H$_9$; R$^1$ is —CH—(CH$_3$)$_2$, C$_6$H$_5$ and —CH$_3$—O—C$_6$H4-; with a proviso that when (n) is 1, then X is =O.

* * * * *